(12) United States Patent
Chorev et al.

(10) Patent No.: US 11,885,810 B2
(45) Date of Patent: Jan. 30, 2024

(54) DETECTION OF MEMBRANE PROTEINS BY MASS SPECTROMETRY

(71) Applicant: OXFORD UNIVERSITY INNOVATION LIMITED, Oxford (GB)

(72) Inventors: Dror S. Chorev, Oxford (GB); Carol V. Robinson, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 509 days.

(21) Appl. No.: 17/272,591

(22) PCT Filed: Aug. 30, 2019

(86) PCT No.: PCT/GB2019/052421
§ 371 (c)(1),
(2) Date: Mar. 1, 2021

(87) PCT Pub. No.: WO2020/049274
PCT Pub. Date: Mar. 12, 2020

(65) Prior Publication Data
US 2021/0325402 A1 Oct. 21, 2021

(30) Foreign Application Priority Data
Sep. 5, 2018 (GB) ..................................... 1814454

(51) Int. Cl.
*G01N 33/68* (2006.01)
*H01J 49/16* (2006.01)
(52) U.S. Cl.
CPC ........ *G01N 33/6848* (2013.01); *H01J 49/165* (2013.01)

(58) Field of Classification Search
CPC ........................... G01N 33/6848; H01J 49/165
See application file for complete search history.

(56) References Cited

U.S. PATENT DOCUMENTS

2011/0097819 A1    4/2011   Groves et al.

FOREIGN PATENT DOCUMENTS

| WO | 2002/056026 A1 | 7/2002 |
| WO | 2014/096821 A1 | 6/2014 |
| WO | 2018/154318 A1 | 8/2018 |

OTHER PUBLICATIONS

Boone et al., Isolation of plasma membrane fragments from HeLa cells. J Cell Biol. May 1969;41(2):378-92.
(Continued)

*Primary Examiner* — Nicole M Ippolito
*Assistant Examiner* — Hanway Chang
(74) *Attorney, Agent, or Firm* — McCarter & English, LLP; Steven G. Davis

(57) ABSTRACT

A method of detecting a membrane protein by mass spectrometry comprises: (a) providing a solution comprising a native membrane vesicle having a lipid bilayer to which said membrane protein is attached; (b) sonicating the vesicle in the presence of a mass spectrometry-compatible buffer; (c) providing a mass spectrometer comprising a nanoelectrospray ionisation source, a mass analyser and a detector; (d) vaporising the sonicated solution using the nanoelectrospray ionisation source under conditions such that the membrane protein is released from the vesicle; (e) ionising the membrane protein; (f) resolving the ionised membrane protein using the mass analyser; and (g) detecting the resolved membrane protein using the detector. Also provided are solutions comprising sonicated vesicles for use in mass spectrometry methods.

19 Claims, 8 Drawing Sheets

(56) References Cited

OTHER PUBLICATIONS

Calabrese et al., Mass spectrometry-enabled structural biology of membrane proteins. Methods. Sep. 1, 2018;147:187-205.
Verkhovskaya, Preparation of Everted Membrane Vesicles from *Escherichia coli*. bio-protocol. Retrieved online at: https://bio-protocol.org/e2254. May 5, 2017;7(9):6 pages.
International Search Report and Written Opinion for Application No. PCT/GB2019/052421, dated Nov. 4, 2019, 10 pages.
Great Britain Office Action for Application No. GB1814454.3, dated May 17, 2019, 4 pages.

DETECTION OF MEMBRANE PROTEINS BY MASS SPECTROMETRY

CROSS-REFERENCE TO RELATED APPLICATIONS

This application is a U.S. national stage filing, under 35 U.S.C. § 371(c), of International Application No. PCT/GB2019/052421, filed on Aug. 30, 2019, which claims priority to United Kingdom Patent Application No. 1814454.3, filed on Sep. 5, 2018.

The project leading to this application has received funding from the European Research Council (ERC) under the European Union's Horizon 2020 research and innovation programme (grant agreement no: 695511).

FIELD OF THE INVENTION

The present invention relates to the detection of membrane proteins. More particularly, the present invention relates to methods for the detection of membrane protein complexes by mass spectrometry. The methods disclosed herein may be used to detect membrane proteins, including complexes of membrane proteins with ligands such as therapeutic agents.

BACKGROUND TO THE INVENTION

Membrane proteins are responsible for a wide range of biological functions. Some of the most prevalent human diseases, including some cancers, result from their dysfunction. Despite representing around a third of the human genome, membrane proteins represent targets for more than half of all current therapeutic agents. As a significant biological target in disease and cancer, their study by traditional structural biology approaches, such as X-ray crystallography and nuclear magnetic resonance, has been hampered by limitations relating to their expression and solubility. Furthermore, X-ray analysis, in the majority of cases, has been limited by crystallographic resolution hindering the assignment of bound moieties.

In contrast to classical structural biology methods, mass spectrometry (MS) is a rapid and sensitive technique that can be used to provide information on intact membrane proteins and their complexes. Membrane protein MS is normally performed using a detergent micelle in which the protein is contained. The membrane protein may be prepared by buffer exchange of the purified protein into an MS-compatible buffer supplemented with the detergent. The micellar solution is vaporised using a nanoelectrospray ionisation source. The membrane protein may then be ionised, resolved and detected by a mass spectrometer.

Analysis of membrane proteins has, so far, required extraction of the membrane proteins from their native membranes—a highly hydrophobic, highly heterogeneous lipid environment—and reconstitution in solution in the presence of chemical detergents. Although the use of solubilising detergents has enabled significant progress to be made in membrane protein MS, membrane proteins may fail to maintain their native properties in the detergent environment. For instance, the stoichiometry, structural conformation and/or functionality of a membrane protein may change.

To overcome these problems, a number of detergent-free methods have been devised. For instance, Hopper et al., Nat Methods 2013, 10 (12), 1206-1208 disclose the use of amiphipols, bicelles and nanodiscs for studying membrane proteins in a detergent-free environment. Marty et al., Angew. Chem. Int. Ed. 2016, 55, 550-554 also use nanodiscs for solubilising membrane proteins in a detergent-free environment. More recently, styrene maleic acid copolymer lipid particles (SMALPs) have also been used (see Postis et al., Biochimica et Biophysica Acta 2015, 1848, 496-501).

However, these approaches generally require high levels of protein expression, thereby restricting their use primarily to proteins of bacterial origin. Moreover, all of these methods have failed to reproduce a native membrane environment. This can be because the methods alter the lipid environment, require the presence of detergents during protein extraction from the membrane, use chemicals that may deform the membrane, have harsh protein size constraints, or are unable to maintain or restore important aspects of the membrane that are crucial for proper protein function, such as membrane curvature.

There exists a need for improved MS methods for detecting membrane proteins, and membrane protein complexes. In particular, there exists a need for MS methods in which the native properties of a membrane protein and its complexes are maintained throughout the method.

SUMMARY OF THE INVENTION

The present invention is based, at least in part, on the surprising discovery that sonication of a vesicle formed from the native membrane of an organism in the presence of a mass spectrometry-compatible buffer gives a solution which can be directly analysed using mass spectrometry. In contrast with previous methods, the present invention enables the membrane protein to be detected while still in its native environment, without the use of detergents or harsh chemicals.

According to a first aspect of the invention there is provided a method of detecting a membrane protein by mass spectrometry, wherein the method comprises:
  (a) providing a solution comprising a native membrane vesicle having a lipid bilayer to which said membrane protein is attached;
  (b) sonicating the vesicle in the presence of a mass spectrometry-compatible buffer;
  (c) providing a mass spectrometer comprising a nanoelectrospray ionisation source, a mass analyser and a detector;
  (d) vaporising the sonicated solution using the nanoelectrospray ionisation source under conditions such that the membrane protein is released from the vesicle;
  (e) ionising the membrane protein;
  (f) resolving the ionised membrane protein using the mass analyser; and
  (g) detecting the resolved membrane protein using the detector.

In further aspects, a solution comprising sonicated native membrane vesicles having a lipid bilayer to which a membrane protein is attached is provided, as is a method for preparing said solution and a solution obtainable by the method. The method comprises (a) providing a solution comprising a native membrane vesicle having a lipid bilayer to which said membrane protein is attached; and (b) sonicating the vesicle in the presence of a mass spectrometry-compatible buffer. In a further aspect of the invention, there is provided the use of the solutions for the detection of membrane proteins by mass spectrometry.

DESCRIPTION OF VARIOUS EMBODIMENTS

Figure 1:
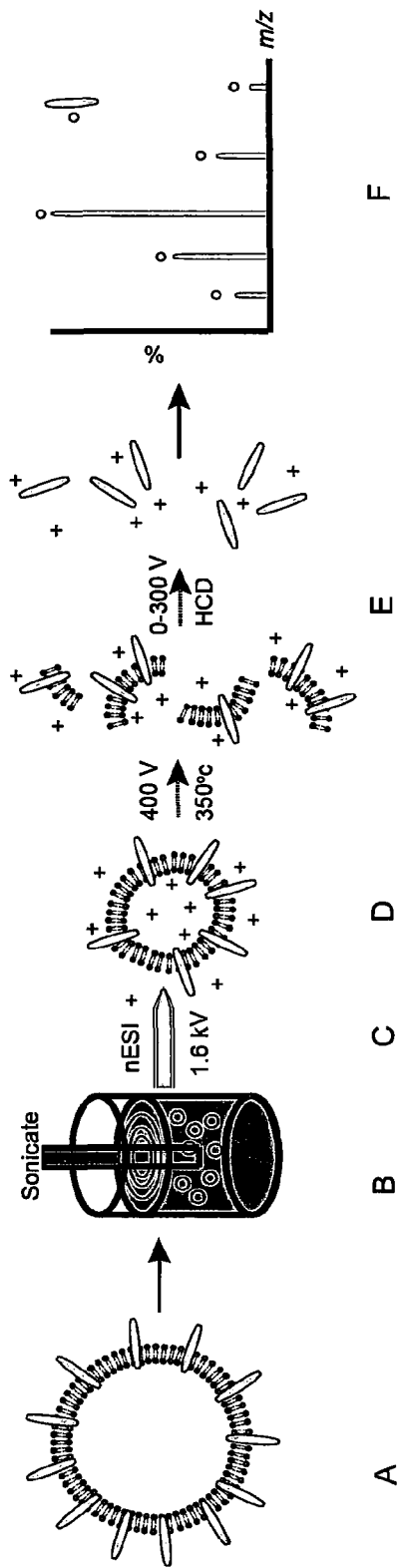
FIG. 1 is a schematic diagram of a sonicated lipid vesicle method of the present invention. According to the exemplified method, a native membrane vesicle having membrane proteins embedded in the lipid bilayer (A) is sonicated (B), then vaporised (C) using nanoelectospray ionisation (nESI). The membrane proteins are ionised (D) and the lipid bilayer removed through high-energy collisional dissociation (HCD) (E). The membrane proteins are resolved and detected using a mass spectrometer. The resulting mass spectrum (F) is shown.

The present invention relates to a method of detecting a membrane protein by mass spectrometry. According to the method, a native membrane vesicle having a lipid bilayer to which the membrane protein is attached is provided.

Vesicles are well-understood in the art to be structures in which a lipid bilayer encloses an interior, typically liquid-filled, space. A native membrane vesicle has a lipid bilayer which is formed from the lipid bilayer that is present in the native environment of the membrane protein, i.e. from the native membrane of an organism. Unlike prior art methods in which a membrane protein is analysed by mass spectrometry, the membrane protein is not extracted from its native membrane. Instead, the membrane protein is preserved in its native membrane environment, and is used in this form in the mass spectrometry solution. This enables the membrane protein to be detected truly in its native state.

Typically, native membranes comprise glycerophospholipids. However, other lipids may also be present in a native membrane, such as phosphatidyl ethanoloamine, phosphatidyl glycerol, cardiolipins, phosphatidylcholines, phosphatidylserine, cholesterol, diacylglycerols, fatty acids and lipopolysaccharides. The lipids that are present in a native membrane may vary. For instance, native membranes derived from bacteria and mitochondria typically contain phosphatidyl ethanoloamine, phosphatidyl glycerol, and cardiolipins. The outer membrane of bacteria contains lipopolysaccharides, usually in high quantities.

The native membrane vesicles may be derived from prokaryotic membranes, such as from bacterial membranes. The native membrane vesicles may also be derived from eukaryotic membranes, such as from cell membranes or organelle membranes. Suitable organelles include mitochondria. Other eukaryotic membranes include membrane discs which may be obtained from the cone of a squid or from bovine eyes.

The native membrane vesicle may be a unilamellar vesicle, i.e. the vesicle contains a single lipid bilayer. However, in some embodiments, the vesicle may be a multilamellar vesicle, i.e. the vesicle contains two or more lipid bilayers, e.g. two lipid bilayers. In these embodiments, the membrane protein is preferably attached to an inner lipid bilayer. Without wishing to be bound by theory, it is believed that the outer lipid bilayer may provide some protection to the inner lipid bilayer during sonication, thereby helping to preserve the membrane protein in an intact state.

The vesicle may be inverted, such that those portions of the membrane protein that are typically on the inner surface of the native membrane are on the outside of the vesicle. However, it is generally preferred for a native membrane vesicle not to be inverted so that any portions of a membrane protein that extend from the inner surface of the native membrane are protected. The orientation of the membrane protein may be controlled by adjusting the conditions of the solution in which the vesicles are prepared, or by adjusting the method by which the membrane protein is prepared.

The solution comprising a native membrane vesicle may be prepared by: (i) providing a native membrane to which said membrane protein is attached; and (ii) preparing the native membrane vesicle from the native membrane, such that the lipid bilayer from the native membrane forms the lipid bilayer in the vesicle.

Methods for preparing native membrane vesicles from native membranes are known in the art. For instance, cells providing the membrane proteins of interest may be obtained, e.g. by culturing cells such as bacterial cells or directly from an organism. The membrane protein in its native membrane may then be separated from other parts of the cell, e.g. by centrifugation methods such as different centrifugation using a sucrose gradient. The separated membranes may be resuspended in a buffer to provide native membrane vesicles comprising the membrane protein. The buffer may be a mass spectrometry-compatible buffer (e.g. as described herein) or it may be another buffer, such as a Tris-buffer. Suitable methods for preparing native membrane vesicles are described in Zeev-Ben-Mordehai et al., Structure 2014, 22(11), 1687-1692. Further examples of suitable methods are disclosed in Baker et al., Methods Enzymol 2015, 557, 307-328; in Hsu et al., J Comput Chem 2017, 38, 2354-2363; and in Maeda et al., Acta Crystallogr Sect F Struct Biol Cryst Commun 2013, 69, 1368-1370. The contents of these documents are incorporated herein by reference.

Membrane proteins can be grouped into integral membrane proteins and peripheral membrane proteins. Integral membrane proteins may have one or more segments embedded within a membrane and may be bound to the lipid bilayer. Peripheral membrane proteins may be temporarily associated with the lipid bilayer and/or integral membrane proteins. In an embodiment, the membrane protein is an integral membrane protein.

Membrane proteins may be composed of one (mono) or more (multi) associated polypeptide chains. Thus, the membrane protein may be a monomeric or a multimeric membrane protein, for example an oligomeric membrane protein. Oligomeric membrane proteins include both homooligomeric (identical polypeptide chains) and heterooligomeric (different polypeptide chains) proteins.

In an embodiment, the membrane protein has a molecular weight of from about $10^3$ Daltons to about $10^{12}$ Daltons, e.g. from about $10^3$ Daltons to about $10^6$ Daltons.

In an embodiment, the membrane protein is an integral membrane protein selected from G protein-coupled receptors (GPCRs), membrane transporters, membrane channels, ATP-binding cassette transporters (ABC-transporters), proton driven transporters, solute carriers, outer membrane proteins (OMPs), ATP synthases, and protein and ligand translocases.

In specific examples, the membrane protein is selected from anchor cell fusion failure protein 1 (AFF-1), β-barrel assembly machinery (BAM), bacterial molecular chaperone DnaK, cytochrome bo3, the CydAB cytochrome bd oxidase complex, energy-transducing Ton complex, multidrug efflux pumps such as AcrABZ-TolC and MdtABCTolC, and ATP synthase, membrane protein complexes in the respiratory chain (e.g. complexes I-V), adenine nucleotide translocase 1 (ANT-1), and subunits thereof.

The membrane protein may be in the form of a complex with a ligand. The present methods may therefore be used to detect binding between a membrane protein and a ligand. In particular, a method of the present invention may allow one or more structural characteristics (e.g. stoichiometry) of a membrane protein-ligand complex to be determined, and/or may also be used to detect conformational changes that take place upon binding of a therapeutic agent to the membrane protein.

Binding of the ligand to the membrane protein may be via a non-covalent or a covalent interaction, though will typically be via a non-covalent interaction. In particular, binding of the ligand to the membrane protein may be via intermolecular forces such as ionic bonds, hydrogen bonds and van der Waals forces. Binding of the ligand to the membrane protein may be reversible or irreversible. In an embodiment, the ligand is bound to the membrane protein via a reversible bond.

Ligands with which the membrane protein may be in the form of a complex include one or more of therapeutic agents, lipids, nucleotides and nucleosides.

In some embodiments, the membrane protein may be in the form of a complex with one or more lipids. Particular examples of lipids include, but are not limited to, fatty acids, glycerolipids, glycerophospholipids, sphingolipids, sterol lipids, prenol lipids, saccharolipids and polyketides.

In one embodiment, the membrane protein is in the form of a complex with one or more therapeutic agents. The therapeutic agent may be an active compound which, when administered to an organism (human or non-human animal), induces a desired pharmacologic, immunogenic, and/or physiologic effect by local and/or systemic action. Examples of therapeutic agents include, without limitation, drugs, vaccines and biopharmaceutical agents. Thus, therapeutic agents may include small molecule drugs, therapeutic proteins, peptides and fragments thereof (whether naturally occurring, chemically synthesised or recombinantly produced), and nucleic acid molecules (including both double- and single-stranded molecules, gene constructs, expression vectors, antisense molecules and the like). Therapeutic agents may also include substrates, inhibitors, activators, neurotransmitters, agonists and antagonists. The therapeutic agent may be a synthetic or naturally occurring compound.

The therapeutic agent may be a drug candidate or other agent suspected of having therapeutic application.

Particular examples of therapeutic agents include, but are not limited to, anti-cancer agents, anti-infective agents (e.g. antibiotics and antiviral agents), analgesic agents, anorexic agents, anti-inflammatory agents, antiepileptic agents, anaesthetic agents, hypnotic agents, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics agents, hormones, nutrients, antiarthritics agents, antiasthmatic agents, anticonvulsants, antihistamines, antinauseants agents, antineoplastic agents, antipruritics agents, antipyretic agents; antispasmodic agents, cardiovascular agents (e.g. calcium channel blockers, beta-blockers, beta-agonists, antiarrhythmic agents, antihypertensive agents, diuretics and vasodilators), central nervous system stimulants; decongestants, hormones, bone growth stimulants, bone resorption inhibitors, immunosuppressive agents, muscle relaxants, psychostimulants, sedatives and tranquilisers. It will be appreciated that this list of therapeutic agents is merely illustrative and should not be considered to be limiting. Many other therapeutic agents are known in the art and may be utilised in a method of the present invention. A detailed description of various therapeutic agents may be found in e.g. Remington's Pharmaceutical Sciences (21st edition, 2005, Mack Publishing Company). The therapeutic agent may exhibit optical isomerism and/or diastereoisomerism. Accordingly, the therapeutic agent may be in the form of a single enantiomer or diastereoisomer, or a mixture (e.g. a racemic mixture) thereof.

In an embodiment, the therapeutic agent has a molecular weight of less than 2000 Daltons, e.g. less than 1500 Daltons, e.g. less than 1000 Daltons, e.g. less than 500 Daltons. In an embodiment, the therapeutic agent is a non-polymeric organic compound having a molecular weight of less than 1000 Daltons, e.g. less than 800 Daltons, e.g. less than 500 Daltons.

In an embodiment, the therapeutic agent is an inhibitor or an activator, e.g. an activator or inhibitor of the membrane protein to which it is bound. In an embodiment, the therapeutic agent is an anti-cancer agent.

A method of the present invention may allow therapeutic agents to be screened. In contrast to indirect methods such as fluorescence or calorimetry, the present method may allow therapeutic agents to be screened directly. In particular, a method may be used to screen for the binding of activators and transporter substrates which are difficult to screen using conventional in vivo methodologies. Moreover, unlike X-ray crystallography, the present methods are not complicated by the inherent structural flexibility of membrane protein-therapeutic agent complexes and may allow the dynamical behaviour of membrane proteins and their interaction with therapeutic agents to be studied.

Where the membrane protein is in the form of a complex with a therapeutic agent, the solution comprising a native membrane vesicle preferably comprises a molar excess of the therapeutic agent as compared to the membrane protein. In an embodiment, the molar ratio of the therapeutic agent to the membrane protein is at least 2:1, e.g. at least 5:1, e.g. at least 10:1. In an embodiment, the therapeutic agent is present in the solution at a concentration of at least 100 nM, e.g. from 100 nM to 900 nM.

Other ligands such as lipids, nucleotides and nucleosides may be in a complex with the membrane protein in its native environment and, as such, will typically not be added to the solution.

The membrane protein may be in the form of a complex with more than one ligand. Thus, for instance, a method of the present invention may be used to determine whether the presence of a first ligand affects binding of a second ligand to the membrane protein.

In embodiments, the native membrane vesicle may comprise at least 2, e.g. at least 3, e.g. at least 4, different membrane proteins. A method of the present invention may be used to detect at least 2, e.g. at least 3, e.g. at least 4, different membrane proteins that are present in the native membrane vesicle.

A key advantage of the present invention is that it does not require the use of detergents at any point during processing, collection or analysis of the membrane protein, which can interfere with the native environment of the membrane protein. Thus, the solution comprising the native membrane vesicle is preferably obtained by a method in which detergents are not used.

The solution comprising the native membrane vesicle preferably comprises detergent at a concentration of less than 100 µM, e.g. less than 1 µM. Preferably, the solution is substantially free from detergent. It will be appreciated that these values also apply to the sonicated solution on which mass spectrometry is conducted.

Though references are made herein to "the native membrane vesicle", it will be appreciated that the solution will typically contain a plurality of native membrane vesicles which comprise the membrane protein.

Once the solution comprising a native membrane vesicle has been provided, it is sonicated in the presence of a mass spectrometry-compatible buffer. Without wishing to be bound by theory, it is believed that sonication temporarily disrupts the native membrane vesicles enabling ingress of the mass spectrometry-compatible buffer into the vesicle. This enables the membrane proteins to be ionised more efficiently.

The vesicle may be sonicated for more than 1 minute. The vesicle may be sonicated for less than 5 minutes. For instance, the vesicle may be sonicated for from 2 to 4 minutes, e.g. from 2 to 3 minutes, e.g. for 2.5 minutes.

The vesicle may be sonicated intermittently, e.g. by cyclically applying and removing ultrasound. For instance, ultrasound may be applied in cycles of 1 to 5 seconds 'on' and 3 to 10 seconds 'off', e.g. 2 to 4 seconds 'on' and 5 to 7 seconds 'off'. When the vesicle is sonicated intermittently, 'off' periods are still taken into account when calculating the time period over which sonication is applied.

Sonication may be applied using a probe sonicator, such as a Vibra-Cell VCX-500 Watt, Sonics.

Sonication may be applied with a power output of at least 200 W, e.g. from 200 to 500 W, e.g. from 250 to 350 W, e.g. 300 W. The frequency may be at least 15 kHz, e.g. from 15 to 30 kHz, e.g. from 18 to 25 kHz, e.g. 20 kHz.

Sonication may be carried out at a temperature of lower than 20° C., e.g. at a temperature of lower than 15° C., e.g. lower than 10° C. In some embodiments, sonication may be carried out on ice. This is to stop the solution from heating up as a result of the sonication.

A wide range of mass spectrometry-compatible buffers may be used in the sonication stage. Suitable buffers include ammonium buffers, such as ammonium acetate or ammonium bicarbonate. Ammonium acetate is a particularly preferred.

The sonicated solution preferably comprises the mass spectrometry-compatible buffer at a concentration of at least 150 mM, e.g. 250 to 1000 mM, e.g. 400 to 600 mM. Typically, the membrane protein will be present in the sonicated solution in an amount of at least 0.5 mg/mL, e.g. from 0.5 to 20 mg/mL, e.g. from 1 to 10 mg/mL. Preferably the pH of the sonicated solution is in the range of from about 5 to about 8.

Where the solution comprising a native membrane vesicle does not contain a mass spectrometry-compatible buffer, then the method of the present invention may comprise resuspending the native membrane vesicles in the mass-spectrometry compatible buffer, or diluting the solution of native membrane vesicles using the mass spectrometry-compatible buffer, before sonication. Further buffer exchange and concentration of the solution may be achieved after sonication using suitable techniques and devices known in the art, e.g. using a concentrating tube such as a concentrating tube with a 10-50 kDa cut-off (Milipore).

Since the membrane protein is preserved in its native membrane, the protein is preferably present in the sonicated solution in an intact, folded state. This may allow the protein to be detected in its folded, i.e. "native", state.

Once the sonicated solution of native membrane vesicles has been prepared, it is used as the solution in a mass spectrometry method. Without wishing to be bound by theory, it is believed that the lipid bilayer in the native membrane vesicle may at least partially shield the membrane protein during the electrospray ionisation process, in particular during the droplet phase of the electrospray ionisation process. The vesicle bilayer may also afford at least partial shielding from ionisation of the membrane protein during this process. The vesicle may exert a pressure sufficient to maintain the structure of the protein, thereby minimising the deleterious effects associated with vaporisation and substantially retaining interactions between the membrane protein and any ligand as well as interactions within any subunits of the protein.

The membrane protein is detected using a mass spectrometer comprising a nanoelectrospray ionisation source, a mass analyser and a detector. The mass spectrometer is preferably adapted to transmit and detect ions having mass-to-charge (m/z) ratios in the range of e.g. from about 100 m/z to about 32,000 m/z. Preferably, the mass spectrometer is operated under conditions suitable for maintaining and focusing large macromolecular ions. By way of illustration, and without limitation, the mass spectrometer may be an orbitrap mass spectrometer, such as a Q-Exactive hybrid quadrupole-orbitrap mass spectrometer (more preferably, an ultra-high mass range (UHMR) spectrometer). The resolution provided by such instruments is particularly suited to resolving peaks generated from complexes comprising membrane proteins bound to ligands. A Synapt (e.g. a Synapt HDMS ion-trap-IM-MS instrument, such as a G1 instrument) or a Q-ToF mass spectrometer can also be used.

The nanoelectrospray ionisation source is used to vaporise the sonicated solution. Nanoelectrospray ionisation is a technique well-known in the art (see e.g. Wilm et al, Anal. Chem. 1996, 68, 1-8; and Wilm et al, Int. J. of Mass Spec. and Ion Proc. 1994, 132, 167-180). The use of nanoelectrospray ionisation allows ions, and in particular highly charged ions, to be generated directly from solution. The formation of highly charged ions may allow the detection of high mass complexes at relatively low mass-to-charge (m/z) ratios. The use of a nanoelectrospray ionisation is also desirable from the point of view of allowing a membrane protein complex, or subunits of a complex, to remain substantially intact. In performing a method of the present invention, it may be preferable to use a nanoflow capillary, e.g. a gold-coated nanoflow capillary, to vaporise the solution.

The sonicated solution is preferably vaporised under conditions such that the lipid bilayer is dissociated from the membrane protein. For instance, the solution is preferably vaporised under conditions such that the membrane protein is released from the vesicle. The lipid bilayer may be may be dissociated from the membrane protein as a result of collisions between the electrospray and the bilayer which serve to disrupt the lipid-protein interactions. Preferably, the vaporisation conditions are selected so that the membrane protein is detected substantially intact. Preferably, the conditions inside the mass spectrometer are selected to rapidly remove the lipid bilayer from the membrane protein.

Ionisation of the membrane protein may occur during the step of vaporising and/or after release of the membrane protein from the vesicle. In some instances, portions of the membrane protein, e.g. hydrophilic/cytoplasmic domains, may become ionised prior to release of the membrane protein from the vesicle. Typically, ionisation of the membrane protein occurs during and/or after dissociation of the lipid bilayer from the membrane protein.

In an embodiment, release and/or ionisation of the membrane protein occurs in a collision cell present within the mass spectrometer. Release and/or ionisation of the membrane protein may be achieved by adjusting acceleration voltages and/or pressures within the collision cell to remove the lipid bilayer while retaining the peaks of the membrane protein.

Mass spectrometer parameters may be optimised for maximal desolvation and bilayer removal, while minimising protein activation. Optimisation of parameters may be achieved by first setting the instrument parameters to relatively high activation settings for membrane proteins. Then iteratively, parameters may be adjusted to produce resolved mass spectra while minimizing over-activation of the target membrane protein.

Preferably, minimal activation energy is used to dissociate the membrane protein from the vesicle. In an embodiment, the laboratory frame energy is from about 500 to about 5000 electron volts, e.g. from about 500 to about 1500 electron volts. The term "laboratory frame energy" as used herein refers to the collision voltage multiplied by charge state of the protein.

In a preferred embodiment, a mass spectrometer is operated under one or more of the following conditions: (i) a desolvation voltage, e.g. a negative desolvation voltage, of from about 100 to about 300 V, e.g. from about 150 to about 250 V, e.g. from about 175 to about 225 V; (ii) a source fragmentation of about 100 to about 300 V, e.g. from about 150 to about 250 V, e.g. from about 175 to about 225 V; and (ii) an acceleration voltage in the higher-energy collisional dissociation (HCD) cell of from about 0 to about 350 V, e.g. from about 0 to about 325 V, e.g. from about 0 to about 300 V. Preferably the mass spectrometer is operated at a minimum power (i.e. the sum of desolvation voltage, source fragmentation and HCD acceleration voltage) of at least 400 V, e.g. at least 500 V, e.g. at least 600 V. The mass spectrometer may be operated at a power of from 600 to 750 V.

The capillary tube of the nanoelectrospray ionisation source may be heated to a temperature of greater than 250° C., e.g. from 250 to 450° C., e.g. from 300 to 400° C., e.g. from 325 to 375° C. These high temperatures assist with protein desolvation and adduct removal whilst leaving the membrane protein largely unaffected.

The mass spectrometer may also be operated under one or more of the following conditions: (iv) a capillary voltage of from about 0.8 to about 2.2 kV, e.g. from about 1.0 to about 2.0 kV, e.g. from about 1.2 to about 1.8 kV; (v) a pressure in the HCD cell of from about $8.0\times10^{-10}$ to about $2.5\times10^{-9}$ mBar, e.g. from about $8.5\times10^{-10}$ to about $2\times10^{-9}$ mBar, e.g. from about $1.5\times10^{-9}$ to about $2\times10^{-9}$ mBar; (vi) an injection flatapole voltage of about 4.0 to about 8.5 V, e.g. about 6.0 to about 8.5 V, e.g. about 7.5 to about 8.5 V; (vii) an inter flatapole lens voltage of about 2.0 to about 7.0 V, e.g. about 4.0 to about 7.0 V, e.g. about 5.0 to about 7.0 V; (viii) a bent flatapole voltage of about 2.0 to about 6.0 V, e.g. about 3.0 to about 5.0 V, e.g. about 3.5 to about 4.5 V; (ix) a C-trap lens tune offset of: 1 to 3 V, e.g. 1.5 to 2.5 V, e.g. 1.75 to 2.25 V; and (x) a threshold of 2 to 4 V, e.g. 2.5 to 3.5 V, e.g. 2.75 to 3.25 V; (xi) a transfer multipole of about 0 to about 5 V, e.g. about 0 to about 3 V, e.g. about 0 to about 1 V, e.g. 0 V; (xii) a transient time of about 20 to about 150 ms, e.g. about 50 to about 130 ms, e.g. about 80 to about 120 ms; (xiii) a noise level parameter of about 2 to about 5, e.g. about 2.5 to about 4, e.g. about 3 to about 3.5; (xiv) a resolution of about 8,000 to about 140,000, e.g. about 10,000 to about 100,000, e.g. about 15,000 to about 30,000; and (xv) a voltage in the C-trap entrance lens of from about 2 to about 10 V, e.g. from about 3 to about 9 V, e.g. from about 5 to about 8 V. Extended mass range (EMR) is preferably set to 'on'. The detector is preferably set to high m/Z.

In these embodiments, the mass spectrometer is preferably an orbitrap mass spectrometer, such as a Q-Exactive hybrid quadrupole-orbitrap mass spectrometer (e.g. available from Thermo Scientific), and preferably is an ultra-high mass range (UHMR) spectrometer. The mass spectrometer may be modified as described in van de Waterbeemd et al., Nat Methods. 2017, 14(3), 283-286, the contents of which is incorporated herein by reference.

A mass spectrometer may also be operated under one or more of the following conditions: (i) a capillary voltage of from about 0.8 to about 2.2 kV, e.g. from about 1.0 to about 2.0 kV, e.g. from about 1.2 to about 1.8 kV; (ii) a cone voltage of from about 100 to about 240 V, e.g. from about 150 to about 230 V, e.g. from about 175 to about 225 V; (iii) a trap collision energy of from about 100 to about 300 V, e.g. from about 150 to about 250 V, e.g. from about 175 to about 225 V; (iv) a transfer voltage of from about 100 to about 300 V, e.g. from about 150 to about 250 V, e.g. from about 175 to about 225 V; (v) a source temperature of from about 50 to about 140° C., e.g. from about 70 to about 110° C., e.g. about 80 to about 100° C.; (vi) a bias voltage of from about 0 to about 50 V, e.g. from about 2 to about 30 V, e.g. from about 3 to about 10 V; and (vii) a backing pressure of from about 1 to about 8 mBar, e.g. from about 5 to about 7 mBar, e.g. from about 5 to about 6 mBar.

In these embodiments, the mass spectrometer is preferably an ion mobility-mass spectrometer, such as a Synapt HDMS ion-trap-IM-MS instrument (more preferably a G1 instrument). Where the membrane protein is detected using ion mobility-mass spectrometry (IM-MS), the mass spectrometer may comprise an ion mobility cell to assess the folded state of protein complexes. The use of IM-MS may allow the stoichiometry of ligand agent binding, and the overall effects of ligand binding on the dynamics, stabilities, oligomeric structures and conformations of proteins, to be determined. For instance, the stoichiometry and oligomeric structure of complexes may be characterised by assessing mass differences. As a further example, dynamics, stabilities and conformations may be characterised by changes in charge states or by differences in arrival time distributions (i.e. ion mobility).

The membrane protein may also be detected using tandem mass spectrometry (MS-MS).

The ionised membrane protein is then resolved and detected and, if desired, further characterised. In particular, in embodiments in which the membrane protein is complexed with a ligand, ions in which the ligand is bound to the membrane protein or a fragment thereof can be detected directly using the mass spectrometer, rather than inferred indirectly from mass spectra of the separate components (ligand and membrane protein). Moreover, where the solution or the complex comprises more than one ligand, the binding of one or more of said components to the membrane protein may be detected simultaneously. For instance, the method may comprise detecting a plurality of ions selected from the group consisting of ions containing the therapeutic agent bound to the membrane protein or a fragment thereof, ions containing one or more additional components (e.g. selected from lipid and nucleotides) bound to the membrane protein or a fragment thereof, and ions in which the therapeutic agent and one or more additional components are bound to the membrane protein or a fragment thereof. Thus, the present methods may be used to detect concomitant binding of the membrane protein with more than one ligand e.g. a therapeutic agent and one or more other species which compete for binding sites. The binding of one or more lipids from the lipid bilayer to the membrane protein, optionally concomitantly with one or more ligands, may also be directly detected.

Methods for the detection of membrane proteins, as well as complexes thereof, by nanoelectrospray ionisation mass spectrometry are disclosed in WO 2012/172378 and WO 2014/096821, the contents of which are incorporated herein by reference.

EXAMPLES

The following non-limiting Examples illustrate the present invention.

Methods

The following materials and methods were employed in the experiments of the Examples.

Preparation of Membrane Protein-Enriched Extracellular Vesicles (MPEEVs)

Membrane protein enriched extracellular vesicles of Anchor Cell Fusion Failure protein 1 (AFF-1) from Syrian hamster BHK-21 cultured cells were prepared according to Hsu et al., J Comput Chem 2017, 38, 2354-2363. Specifically, BHK-21 cells were grown in Glasgow MEM containing 10% FBS, 20 mM HEPES and 2% triptose phosphate broth at 37° C., 5% $CO_2$. 24 h before transfection, $15 \times 10^6$ cells were seeded onto a T175 cell culture flask. Cells were transfected using 60 µg of selected DNA utilizing Lipofectamine 2000 according to the manufacturer's protocol. 2 h post transfections, cells were washed with PBS and media was changed with 2% FBS in GMEM. 24 h after transfection cells were washed and the medium was replaced with serum free GMEM. 2 days following transfection, medium was collected and centrifuged at 30,000 rpm in a Beckman ultracentrifuge utilizing an SW32Ti rotor. The supernatant was then removed and vesicles were allowed resolubilize in 500 mM ammonium acetate at pH=7.6.

Preparation of *E. coli* Outer and Inner Membrane Vesicles

Outer and inner membranes were prepared following previous reported methods (Baker et al., Methods Enzymol 2015, 557, 307-328). Briefly, 0.5 L *E. coli* BL21 was grown in LB to OD 2.0 at 37° C. with 250 rpm shaking, before harvesting the cells by centrifugation at 4000×g for 10 min. Cells were resuspended in lysis buffer (50 mM Tris pH 7.4, 150 mM NaCl) and lysed with a constant flow cell disruptor at 8-12 kpsi. Cell debris was removed by centrifugation at 4000×g for 10 min, and membranes were harvested by ultracentrifugation in a Beckman SW32Ti rotor for 1 hr at 25000 rpm. The supernatant was removed and the membranes were resuspended in 5.8 mL of lysis buffer with 20% sucrose, before layering on a discrete sucrose gradient in lysis buffer (0.85 mL 55% sucrose, 11.4 mL 51% sucrose, 11.4 mL 45% sucrose, 7.8 mL 36% sucrose) and centrifuging for 17 h at 30000 rpm in the SW32Ti rotor. Outer and inner membranes were removed from the interface of the 55% and 51% and 45% and 36% sucrose layers respectively and washed twice in ~38 mL lysis buffer without sucrose by centrifuging at 25000 rpm for 1 hr in the SW32Ti. The membrane vesicles were resuspended in 0.5-1 mL lysis buffer and stored at 4° C. until further use.

Preparation of Mitochondrial Inner Membranes

Mitochondrial inner membranes were prepared as previously described in Maeda et al., Acta Crystallogr Sect F Struct Biol Cryst Commun. 2013, 69(12), 1368-1370. In brief, after careful removal of fat and connective tissues, bovine heart muscle of one fresh bovine heart was minced using a commercial meat mincer. A 600 g portion of minced meat was suspended on ice in 2,650 mL of 18 mM sodium phosphate buffer, pH 7.4, and homogenized for 10 min at 11,000 rpm in a Polytron PT31 OOD homogenizer, followed by centrifugation for 20 min at 2,800 rpm in a large-scale refrigerated centrifuge (Hitachi himac CR20G) using an R9A rotor at 4 degree Celsius. All of the supernatants were combined and centrifuged for 25 min at 4 degree Celsius and 8,000 rpm in a 30 Hitachi Himac CR20G centrifuge using a R12AF rotor. The precipitate, suspended in 40 mM HEPES buffer (pH 7.8), 0.5 mM EGTA/EDTA and 1 mM DTT, was centrifuged for 30 min at 30,000 rpm in a P45AT rotor using a Hitachi Himac CP80WX ultracentrifuge. Finally, the membrane vesicles were suspended in 40 mM HEPES buffer (pH 7.8), 2 mM $MgCl_2$, 0.5 mM EGTA/EDTA, 1 mM DTT, and the protein concentration adjusted to 26.8 mg/ml.

Preparation of Vesicles from Intact Mitochondria

Mitochondrial membranes were prepared as previously described in S. Yoshikawa et al., Biochim Biophys Acta 2012, 1817, 579-589. In brief, bovine heart muscle of one fresh bovine heart after careful removal of fat and connective tissues was minced to prepare 1000 g of minced meat, and a 500 g portion was suspended in 3250 mL of 23 mM sodium phosphate buffer, pH 7.4, at 0° C. and homogenized for 5 min at 13000 rpm in a homogenizer (Nihon Seiki), followed by centrifugation for 20 min at 2800 rpm in a large-scale refrigerated centrifuge (Kubota Model 9810) using an RS-6600 rotor. The other 500 g portion was also treated with the same procedure. The combined precipitate was suspended in 3375 mL of 22.2 mM sodium phosphate buffer, pH 7.4, and rehomogenized, followed by centrifugation with the same procedure as before. All of the supernatants were combined and centrifuged for 30 min at 10000 rpm with a refrigerated centrifuge, Beckman Model Avanti HP-301 using a JLA-10.500 rotor. The precipitate, suspended in 50 mM Tris-HCl buffer, pH 8.0, was centrifuged for 30 min at 30000 rpm with an ultracentrifuge, Beckman Model-7, using a 45 Ti rotor. The membrane vesicles were suspended in 50 mM Tris-HCl buffer, pH 8.0, containing 660 mM sucrose, adjusting the protein concentration at 23 mg/mL.

Sonication of Membranes for Native Mass Spectrometry

Collected vesicles were diluted in 20 ml of 500 mM ammonium acetate, and sonicated using a probe sonicator (Vibra-Cell VCX-500 Watt, Sonics) using maximal amplitude (60%, i.e. 300 W) for 2.5 min at cycles of 3 seconds on/6 seconds off. Volume was then reduced to ~200 microliters using a 10-50 kDa cut-off concentrating tube (Milipore).

Native Mass Spectrometry

Native mass spectrometry experiments were carried out on a Q-Exactive Plus UHMR modified to facilitate the transmission of high-energy species and adapted for membrane proteins as described in van de Waterbeemd et al., Nat Methods. 2017, 14(3), 283-286. The following parameters were used: Capillary Voltage of 1.6 kV, Dessolvation voltage of 200 V, Source fragmentation of −200 V, HCD energy of 0-300 V. HCD pressure was set to 6, the equivalent of $1.8 \times 10^{-9}$ bar. EMR was set to on, C-trap entrance lens tune offset was set to 2, injection flatapole was set to 8 V, inter flatapole lens was at 6 V, and bent flatapole at 4 V. Threshold was set to 3. Data was analysed using Xcalibur 2.2 (Thermo Fischer) and Masslynx 4.2 (Waters).

Example 1: Detection of Anchor Cell Fusion Failure Protein 1 (AFF-1) Protein

Figure 2:
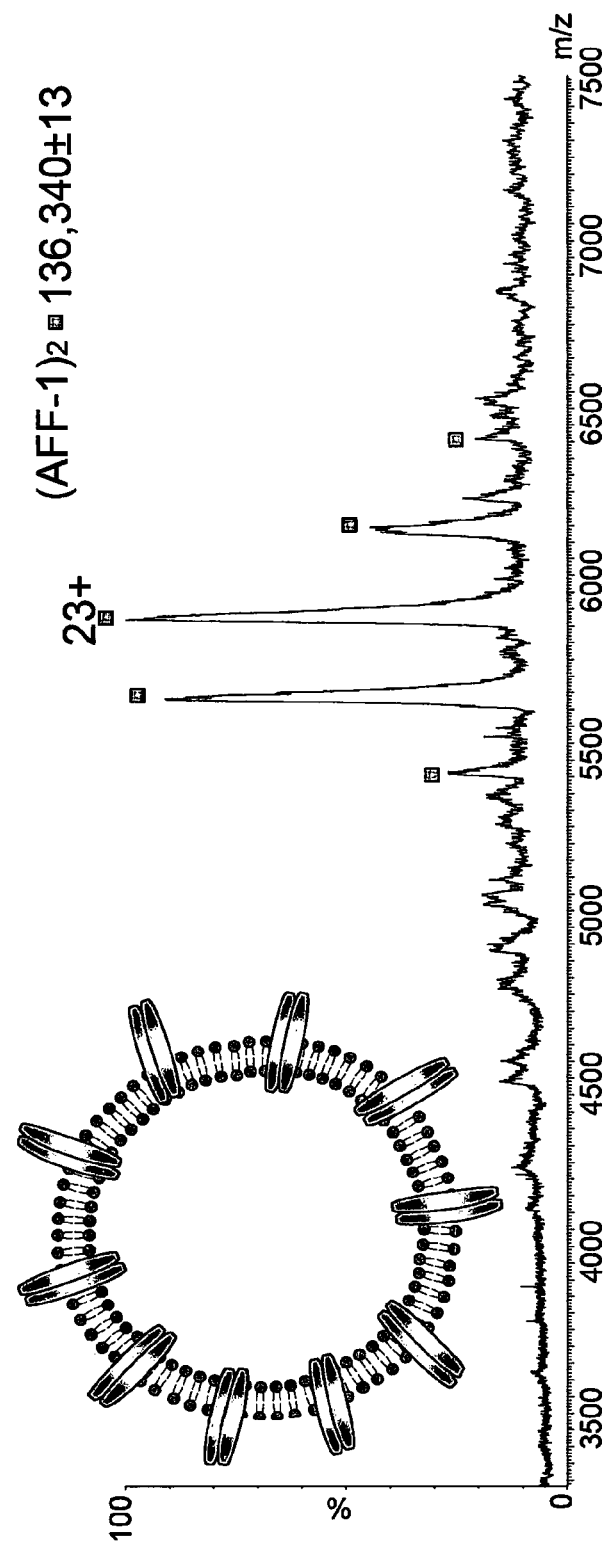
FIG. 2 depicts a nESI mass spectrum of an intact AFF-1 complex released from sonicated membrane protein enriched extracellular vesicles (MPEEVs).

Membrane protein enriched extracellular vesicles (MPEEVs) of anchor cell fusion failure protein 1 (AFF-1) were prepared from Syrian hamster BHK-21 cultured cells. The MPEEVs were diluted in ammonium acetate and sonicated. The sonicated vesicles were vaporised by nESI and the proteins transferred into a modified Q-Exactive orbitrap mass spectrometer. The mass spectrum of AFF-1 released from the sonicated vesicles is shown in FIG. 2.

It can be seen that intact dimeric AFF-1 was released directly from the sonicated vesicles and detected using the mass spectrometer.

Example 2: Detection of Proteins from the Inner and Outer Membrane of E. coli

Outer and inner native E. coli membranes vesicles were prepared. The vesicles were then diluted in ammonium acetate and sonicated. The sonicated vesicles were vaporised by nESI and the proteins transferred into a modified Q-Exactive orbitrap mass spectrometer. Mass spectra of the membrane protein complexes released from the sonicated outer membrane vesicles and inner membrane vesicles are shown in FIGS. 3 and 4, respectively.

Figure 3:
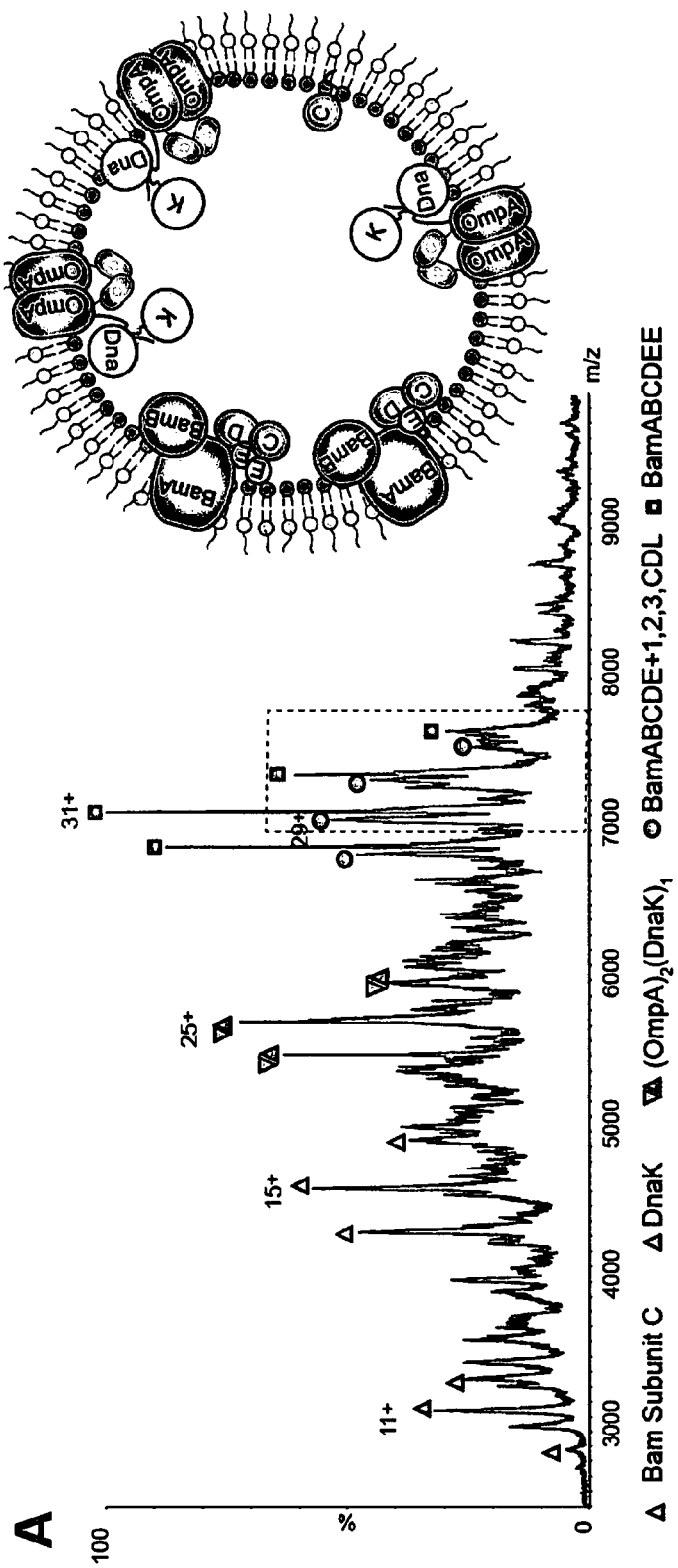
FIG. 3 depicts nESI mass spectra of membrane proteins released from native $E.$ $coli$ outer membrane vesicles. Specifically, the figure shows: A) a mass spectrum in which subunit c of a Bam complex, DnaK, DnaK-OmpA complexes, and two states of the Bam complex are observed; and B) a mass spectrum in which BamABCDE complexed with 1, 2 or 3 cardiolipin (CDL) molecules, and BamABCDEE are observed.
Figure 3:
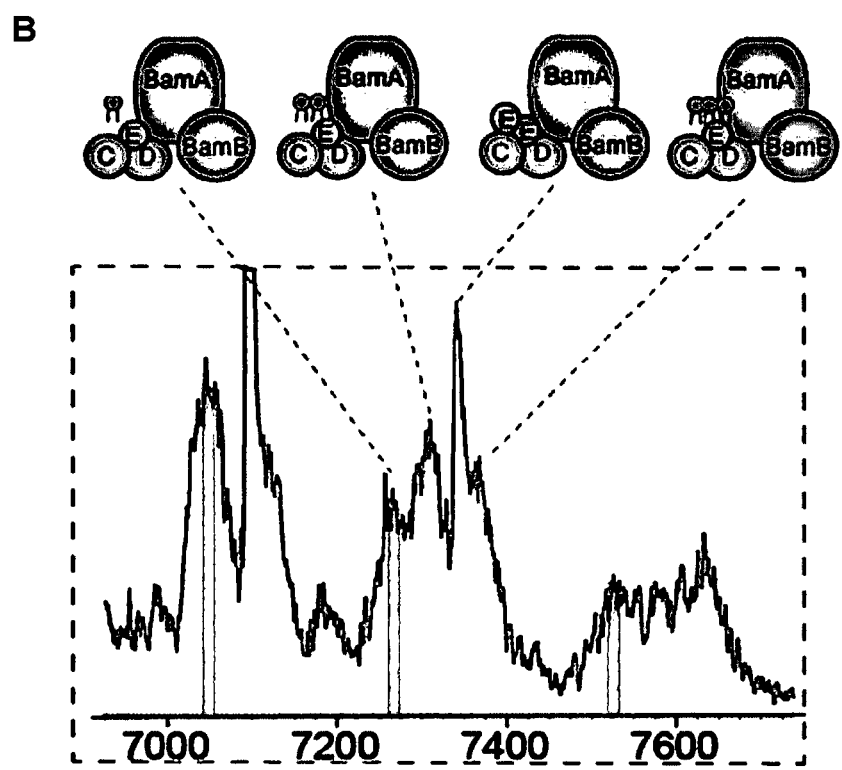
Figure 4:
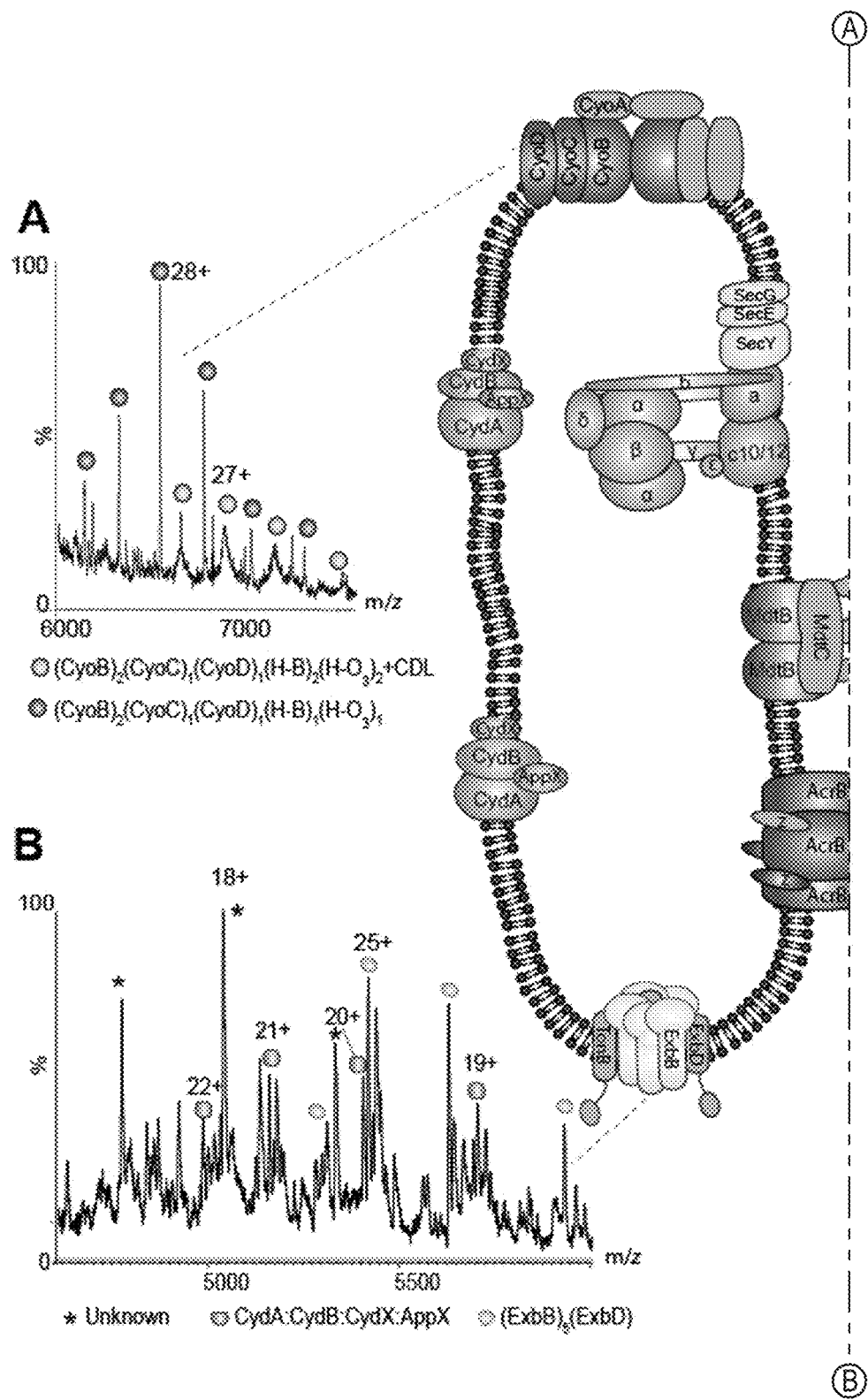
FIG. 4 depicts nESI mass spectra of membrane proteins released from native $E.$ $coli$ inner membrane vesicles. Specifically, the figure shows: A) a mass spectrum in which cytochrome bo3 protein complexes are observed; B) a mass spectrum in which cytochrome bd oxidase protein complexes and Ton multi-drug transporter protein complexes are observed; and C) mass spectra in which multidrug efflux pumps AcrABZ and MdtABC and intact ATP synthase are observed.
Figure 4:
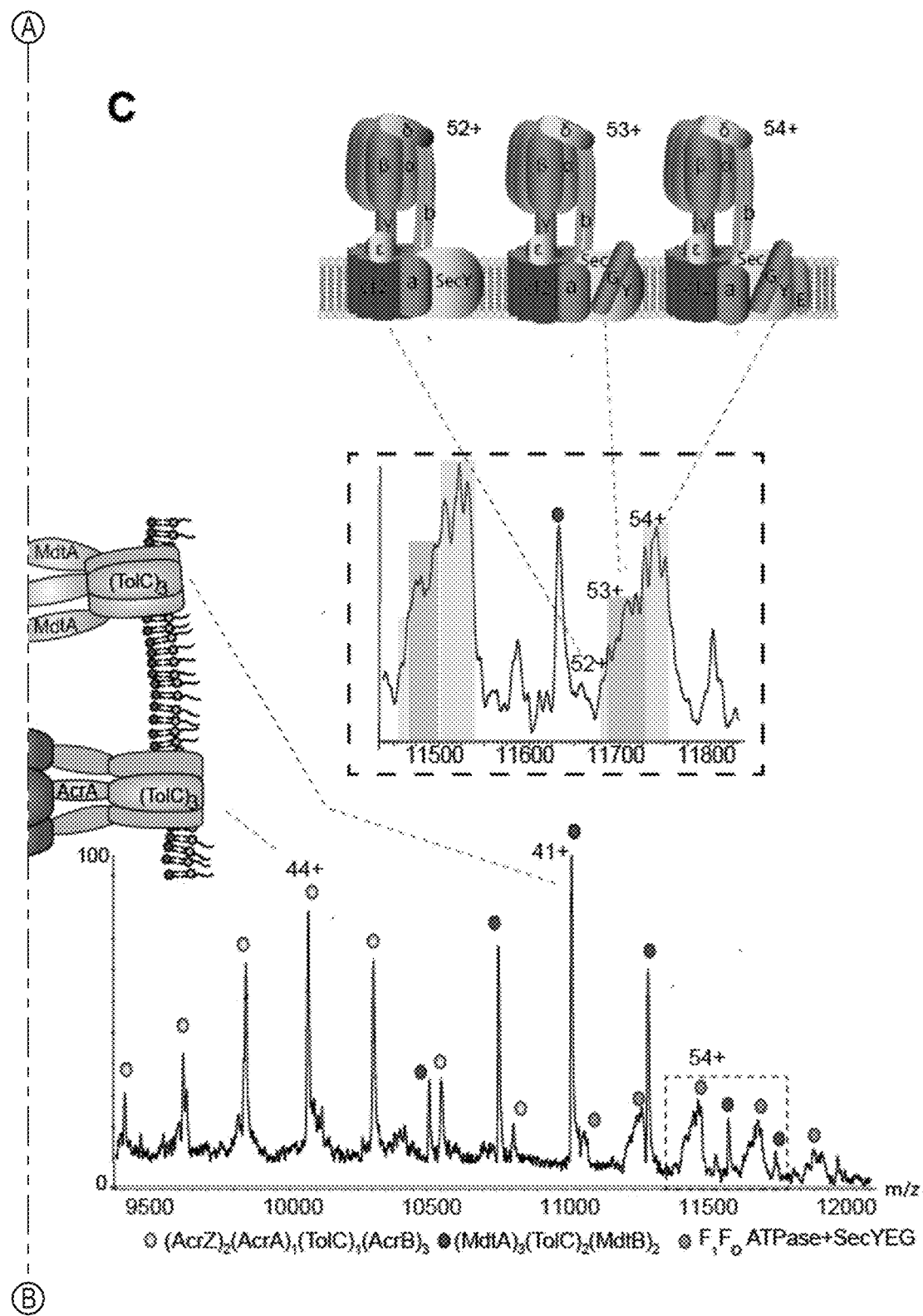

Proteins from E. coli Outer Membrane Vesicles (FIG. 3)

Starting from the low m/z range of the E. coli outer membrane spectrum, species were detected and assigned to BamC with a lipid anchor, a component of the β-barrel assembly machinery (BAM). A high population of DnaK was also observed, a membrane protein previously implicated in outer membrane porin assemblies. DnaK was also detected in the form of a complex with OmpA. Previous reports that DnaK co-immunoprecipitated with full-length pro-OmpA, but not with pro-OmpA(Δ3), implied that sequences outside the β-barrel are required to maintain accessibility of DnaK binding sites. The data obtained in this experiment are consistent with ATP-bound DnaK binding to pro-OmpA but also associating with a second OmpA, likely through the C-terminal dimerisation domain, to form OmpA:proOmpA:DnaK:ATP.

Turning to the high m/z region of the mass spectrum, a high-intensity series of peaks was assigned to BAM. Previous structural studies, following detergent extraction and overexpression of all five subunits on a single plasmid yielded a stoichiometry of 1:1:1:1:1 for Bam subunits A-E. However, using native membrane mass spectrometry, a hexameric complex was predominantly released with a subunit composition of $ABCD(E)_2$. A second lower intensity series was assigned to pentameric Bam ABODE complex, its diffuse peaks consistent with binding of up to three cardiolipin (CDL) molecules.

Based on the information provided by the mass spectrometry results, molecular dynamics simulations were carried out to confirm the stability of the detected complexes. Since NMR solution studies had previously suggested the existence of BamE in the form of a dimer, a molecular dynamics simulation was used to test, and confirmed, the stability of a BamE dimer docked into a Bam ABCD complex. The lipid binding preferences of BamE were also explored, and showed up to three CDL lipids making contact with BamE within the BamABCDE complex, in line with the stoichiometry of CDL binding defined by MS. CDL attachment, via BamE, likely anchors the BamABCDE complex to a region of the E. coli outer membrane high in CDL and conceivably contributes to a membrane targeting mechanism.

Proteins from E. coli Inner Membrane Vesicles (FIG. 4)

E. coli inner membranes contain a minimum of 42 different proteins and, as such, their analysis represents a significant challenge.

For cytochrome bo3, peaks are observed corresponding to $(CyoB)_2(CyoC)_1(CyoD)_1$, with and without one or two $HemeO_3$/HemeB factors, and CDL binding (diffuse peaks). A decrease in charge state of the diffuse peaks implies that lipid binding stabilizes the structure. These results are consistent with the previously proposed CyoB subunit dimer association for cytochrome bo3 in native membranes. A second cytochrome in the inner membrane is assigned as the CydAB cytochrome bd oxidase complex with extensive peak splitting attributed to different Heme groups (B558, B595) and ubiquinol. Both CydX and the paralogous small transmembrane protein AppX are known have the potential to interact with the CydAB complex and have overlapping cellular functions. Native membrane mass spectra showed that CydX and AppX were able to interact simultaneously with CydAB to form a heterotetramer.

Parts of the energy-transducing Ton complex located within the inner membrane were also assigned (the Ton system coupling the outer and inner membranes of E. coli). In the inner membrane three integral membrane proteins are known reside: ExbB, ExbD and TonB. Previous x-ray crystallography and electron microscopy studies had given conflicting results about the assemblies of these integral membrane proteins in the inner membrane. The native mass spectrum confirmed the existence of a pentameric ExbB pore within the native membrane, with trapping of one ExbD protomer within the compact globular complex.

At the higher m/z region, sub-assemblies of multidrug efflux pumps were detected, including AcrABZ-TolC and the less well characterised but related pump MdtABCTolC. Both of these pumps are known to span the inner and outer membranes of E. coli. For AcrABZ-TolC, all three inner membrane subunits (AcrB) are preserved in the mass spectra, and are detected bound to the small subunit (AcrZ) that has only recently been discovered. One copy of the outer membrane protein TolC is bridged by a single copy of the periplasmic subunit AcrA to the inner membrane complex yielding $AcrB_3$:$AcrZ_2$:AcrA:TolC. In the case of MdtABC-TolC, dimeric MdtB remains assembled with $(MdtA)_3$ and $(TolC)_2$ from the outer membrane $(MdtB_2MdtA_3$:$TolC_2)$. Since all three MdtA subunits remain attached, they are likely supported by dimeric MdtB in the inner membrane. This is consistent with the previously reported role of MdtC in substrate binding, rather than in supporting periplasmic subunits. The fact that both AcrABZ-TolC and MdtABC- TolC complexes or sub-assemblies survived the native mass spectrometry process of the present invention, shows that the effects of drugs, e.g. antibiotics, on these multidrug resistance pumps may be studied.

At the highest m/z values, intact ATP synthase consisting of $F_O$ and $F_1$ regions was detected. Peak splitting due to ATP/ADP binding was observed, as well as dissociation of subunits with the mass of the $F_O$ c-subunit. Mass differences between populations were assigned to binding of SecE, Y and G, consistent with SecYEG remaining in contact with the $F_1F_O$ATP synthase as reported previously for insertion of the $F_O$ a-subunit. It could therefore be concluded that, in the native membrane, interactions between $F_OF_1$-ATPase and SecYEG are maintained following insertion in the membrane. Based on the mass spectrometry data, the stoichiometry of the $F_O$ ring was determined. Previously, c-subunits in $F_O$ were lost during detergent extraction or filtered out in other methods. However, the mass spectrometry method of the present invention confirmed the $F_O$ ring consists of 12 c-subunits.

Example 3: Detection of Proteins from the Inner Mitochondrial Membrane of *Bos taurus*

Inner mitochondrial membranes vesicles and vesicles obtained from intact mitochondria (i.e. without separation of the inner and outer membrane) from *Bos taurus* were prepared. The vesicles were then diluted in ammonium acetate and sonicated. The sonicated vesicles were vaporised by nESI and the proteins transferred into a modified Q-Exactive orbitrap mass spectrometer. Mass spectra of the membrane protein complexes released from the sonicated inner mitochondrial membrane vesicles and from intact mitochondrial membrane vesicles are shown in FIGS. 5 and 6, respectively.

Figure 5:
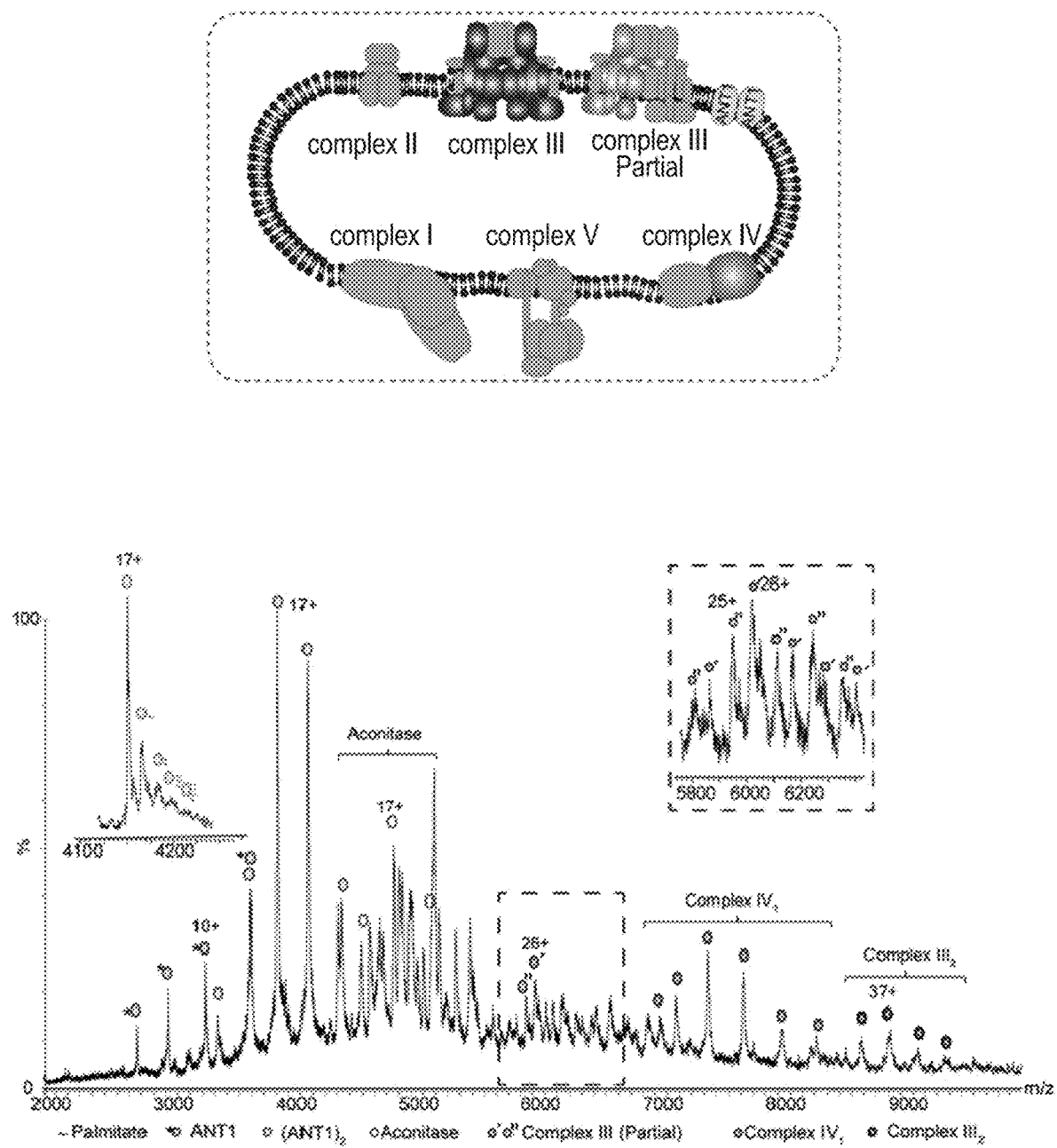
FIG. 5 depicts a nESI mass spectrum of membrane proteins released from inner mitochondrial membrane vesicles. The figure shows a mass spectrum in which palmitate anions bound to the dimer of ANTI are observed, as well as peaks assignable to Complexes III and IV and aconitase.
Figure 6:
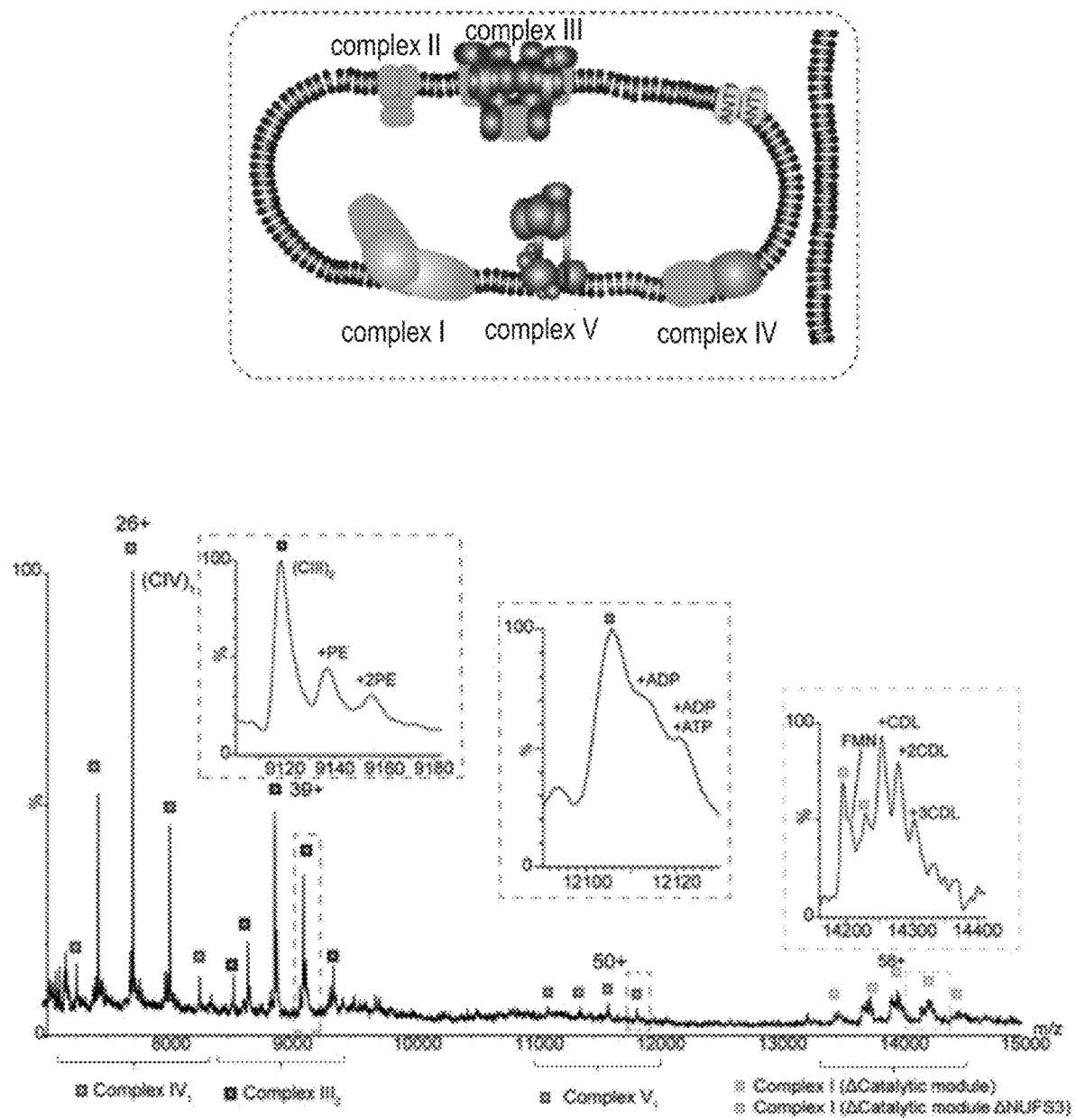
FIG. 6 depicts a nESI mass spectrum of membrane proteins released from native membrane vesicles obtained from intact mitochondria. Lipid bound sub-assemblies of Complex I, Complex IV, and intact Complex V bound to nucleotides are observed.

Proteins from Inner Mitochondrial Membrane Vesicles (FIG. 5)

Inner mitochondrial membranes are densely populated with protein complexes responsible for control of the proton gradient and oxidative phosphorylation between the intermembrane space and the inner mitochondrial matrix.

A number of complexes in the respiratory chain are identifiably in the mass spectra. Specifically, monomeric complex IV with lipid and cofactor occupancy and dimeric complex III, with seven core subunits confirmed by dissociation of cytochrome b and UQCRB, were detected. The most abundant protein in the mass spectrum of the inner mitochondrial membrane was the adenine nucleotide translocase 1 (ANT-1). The stoichiometry and function of ANT-1 has remained controversial with both monomeric and dimeric structures of ANT-1 and UCP2 previously reported. Using the mass spectrometry method of the present invention, the stoichiometry of ANT-1 was revealed as predominantly dimeric, with low occupancy binding of a number of saturated fatty acids (palmitate anions) indicative of a transport mechanism rather than specific binding interaction.

Based on the information provided by the mass spectrometry results, molecular dynamics simulations were carried out to confirm the stoichiometry and function of ANT-1. The simulations showed that tightly bound dimers rapidly formed primarily, but not exclusively, if CDL was present in the inner leaflet of the membrane. Fatty acid binding was also observed with the palmitate head group buried between two helices in each subunit (Y132 and F177). In-situ binding of multiple palmitate anions within the dimer ejected from the native mitochondrial membrane provides direct evidence in support of the role of this fatty acid in the control of uncoupling through ANT-1 transport.

Proteins from Intact Mitochondrial Membrane Vesicles (FIG. 6)

Since complexes I and V were largely absent from the spectra of inner mitochondrial membranes, the method of the present invention was applied to membrane vesicles obtained from intact mitochondria.

Once again, ANT-1 bound to palmitate (not shown) was observed. However, in this case, lipid bound sub-assemblies of Complex I, a Complex IV dimer and intact Complex V bound to nucleotides were detected. This suggests that, by obtaining the membrane vesicles from intact mitochondria, the inner mitochondrial membrane may be prevented from becoming inverted, thereby reducing the impact of sonication on portions of membrane proteins that typically reside in the internal mitochondrial environment.

The invention claimed is:

1. A method of detecting a membrane protein by mass spectrometry, wherein the method comprises:
    (a) providing a solution comprising a native membrane vesicle having a lipid bilayer to which said membrane protein is attached;
    (b) sonicating the vesicle in the presence of a mass spectrometry-compatible buffer;
    (c) providing a mass spectrometer comprising a nanoelectrospray ionisation source, a mass analyser and a detector;
    (d) vaporising the sonicated solution using the nanoelectrospray ionisation source under conditions such that the membrane protein is released from the vesicle;
    (e) ionising the membrane protein;
    (f) resolving the ionised membrane protein using the mass analyser; and
    (g) detecting the resolved membrane protein using the detector.

2. The method according to claim 1, wherein the membrane protein is an integral membrane protein preferably selected from G protein-coupled receptors, membrane transporters, membrane channels, ATP-binding cassette transporters, proton driven transporters, solute carriers and outer membrane proteins.

3. The method according to claim 1, wherein the native membrane vesicle is a unilamellar vesicle.

4. The method according to claim 1, wherein the native membrane vesicle is a multilamellar vesicle with the membrane protein preferably attached to an inner lipid bilayer.

5. The method according to claim 1, wherein the native membrane vesicle is derived from prokaryotic membranes or from eukaryotic membranes.

6. The method according to claim 1, wherein the solution is an aqueous solution preferably comprising detergent at a concentration of less than 100 μM, e.g. less than 1 μM, and more preferably is substantially free from detergent.

7. The method according to claim 1, wherein the membrane protein solution comprising a native membrane vesicle is obtained using a method in which detergents are not used.

8. The method according to claim 1, wherein the method further comprises preparing the solution comprising a native membrane vesicle by: (i) providing a native membrane to which said membrane protein is attached; and (ii) preparing the native membrane vesicle from the native membrane, such that the lipid bilayer from the native membrane forms the lipid bilayer in the vesicle.

9. The method according to claim 8, wherein step (ii) comprises: obtaining cells containing the membrane protein;

separating the membrane protein and its native membrane from other parts of the cell; and suspending the separated membrane in a buffer to provide a solution comprising the native membrane vesicle.

10. The method according to claim 1, wherein the step of sonicating the vesicle comprises sonicating the vesicle for more than 1 minute, and preferably less than 5 minutes, e.g. from 2 to 4 minutes, e.g. from 2 to 3 minutes, e.g. for 2.5 minutes.

11. The method according to claim 1, wherein the step of sonicating the vesicle comprises sonicating the vesicle intermittently by cyclically applying and removing ultrasound, e.g. by applying ultrasound in cycles of 1 to 5 seconds 'on' and 3 to 10 seconds 'off', e.g. 2 to 4 seconds 'on' and 5 to 7 seconds 'off'.

12. The method according to claim 1, wherein the step of sonicating the vesicle comprises:
applying a power of at least 200 W, e.g. from 200 to 500 W, e.g. from 250 to 350 W, e.g. 300 W; and/or
applying a frequency of at least 15 kHz, e.g. from 15 to 30 kHz, e.g. from 18 to 25 kHz, e.g. 20 kHz,
to the vesicles.

13. The method according to claim 1, wherein the mass spectrometry-compatible buffer is ammonium acetate.

14. The method according to claim 1, wherein the mass spectrometer is operated under one or more of the following conditions:

(i) a desolvation voltage of from about 100 to about 300 V, e.g. from about 150 to about 250 V, e.g. from about 175 to about 225 V;
(ii) a source fragmentation of about 100 to about 300 V, e.g. from about 150 to about 250 V, e.g. from about 175 to about 225 V; and
(ii) an acceleration voltage in the higher-energy collisional dissociation (HCD) cell of from about 0 to about 350 V, e.g. from about 50 to about 325 V, e.g. from about 100 to about 300 V.

15. The method according to claim 1, wherein the mass spectrometer is operated at a minimum power of at least 400 V, e.g. at least 500 V, e.g. at least 600.

16. The method according to claim 1, wherein the capillary tube of nanoelectospray ionisation source is operated at a temperature of greater than 250° C., e.g. from 250 to 450° C., e.g. from 300 to 400° C., e.g. from 325 to 375° C.

17. The method according to claim 1, wherein the membrane protein is in the form of a complex with one or more ligands preferably selected from therapeutic agents, lipids, nucleotides and nucleosides.

18. The method according to claim 1, wherein the membrane protein is released from the vesicle substantially intact.

19. The method according to claim 1, wherein the structure or conformation of the membrane protein is characterised.

* * * * *